United States Patent [19]

Kearns et al.

[11] Patent Number: 4,840,905
[45] Date of Patent: Jun. 20, 1989

[54] PROCESS FOR CULTURING BIOLOGICAL MATERIAL

[75] Inventors: Michael J. Kearns, Salisbury, England; Michael J. Comer, Bernried, Fed. Rep. of Germany

[73] Assignee: Boehringer Mannheim GmbH, Mannheim, Fed. Rep. of Germany

[21] Appl. No.: 106,115

[22] Filed: Oct. 7, 1987

[30] Foreign Application Priority Data

Oct. 8, 1986 [DE] Fed. Rep. of Germany ....... 3634203

[51] Int. Cl.$^4$ .................................................. C12N 5/02
[52] U.S. Cl. .............................. 435/240.25; 435/286; 435/315; 435/316; 261/84
[58] Field of Search ............. 435/315, 316, 305, 307, 435/308, 312, 286, 309, 285, 240, 241, 243, 240.25, 240.1, 240.24, 240.46; 366/102, 103, 104, 315, 343, 147, 325, 329, 330, 279; 261/83, 84, 85; 210/178, 179, 219

[56] References Cited

U.S. PATENT DOCUMENTS

| 697,152 | 4/1902 | Lippold | 366/329 X |
| 2,361,503 | 10/1944 | Schutte et al. | 366/329 X |
| 2,740,558 | 4/1956 | Steele | 366/315 X |
| 3,445,342 | 5/1969 | Freedman | 435/316 X |
| 3,623,977 | 11/1971 | Reid | 210/178 X |
| 3,659,827 | 5/1972 | Fogt | 366/315 |
| 3,933,585 | 1/1976 | McAleer et al. | 435/284 X |
| 4,172,034 | 10/1979 | Carlsson et al. | 210/178 |
| 4,343,904 | 8/1982 | Birch et al. | 345/315 X |
| 4,368,174 | 1/1983 | Valyocsik | 366/279 X |
| 4,519,959 | 5/1985 | Takeuchi et al. | 435/315 X |
| 4,670,397 | 6/1987 | Wegner et al. | 435/315 X |

FOREIGN PATENT DOCUMENTS

| 0053869 | 6/1982 | European Pat. Off. | |
| 1293829 | 6/1961 | France | 261/84 |
| 89558 | 6/1937 | Sweden | 210/179 |
| 6596615 | 3/1978 | U.S.S.R. | 435/315 |

OTHER PUBLICATIONS

Katinger et al., "Mass Cultivation and Production of Animal Cells", *Animal Cell Biotech.* 1, 167–169 (1985).

Primary Examiner—Albert J. Makay
Assistant Examiner—Carl D. Price
Attorney, Agent, or Firm—Felfe & Lynch

[57] ABSTRACT

A process for culturing biological material capable of multiplication, especially cells securely adhering to microcarriers, employs a bioreactor having a vessel for a culture medium having means for controlling the environmental conditions in the culture medium and a stirring device for the homogeneous distribution of the cells in the culture medium which has a rotary drive and a rotation axle running in the interior of the vessel, wherein the stirring device has at least one flat stirrer blade fixed on to the rotation axle and inclined to the rotation axle.

13 Claims, 1 Drawing Sheet

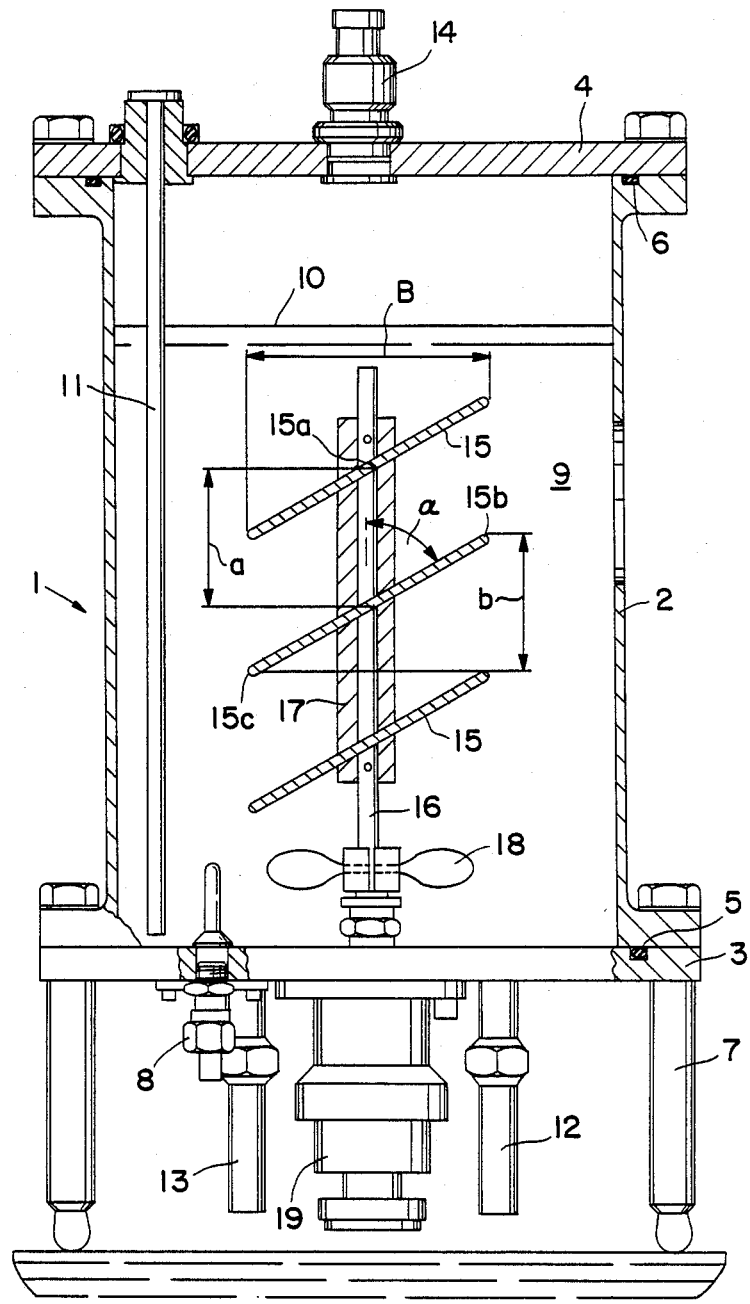

PROCESS FOR CULTURING BIOLOGICAL MATERIAL

The present invention is concerned with a bioreactor for culturing biological material capable of multiplication, especially cells securely adhering to microcarriers, with a vessel for a culture medium having means for controlling the environmental conditions in the culture medium and a stirring device for the homogeneous distribution of the cells in the culture medium which has a rotary drive and a rotation axle running in the interior of the vessel.

In the case of the biotechnical production of substances, especially of proteins for pharmaceutical or medical diagnostic purposes, the appropriate biological materials from which the products are to be obtained are multiplied in a culture medium in an appropriate bioreactor which is often also called a fermenter.

The biomaterial usually consists of micro-organisms or of animal, human or plant cells or of hybrid cells. Whereas, in general, the micro-organisms do not require any carrier material, in many cases the cells can only be cultured on an appropriate carrier material. In this case, one speaks of adherent cells.

The present invention is especially directed to cell cultures in which adherent cells adhere to very small spheroids, for example of dextrant, which are called microcarriers. For the sake of simplicity, in following, reference is made only to the culturing of cells. However, the general applicability of the present invention to other biological materials is thereby not to be limited in any way.

Bioreactors have devices for controlling the environmental conditions (for example oxygen partial pressure, temperature and nutrient material concentration) and for keeping them in a range in which the culture multiplies as intensively as possible. These conditions, as well as the density of the cells in the culture medium, should be as equal as possible throughout the bioreactor, i.e. it is very important for the growth of the culture that a homogeneous distribution of the cells in the culture is achieved.

For this purpose, stirring devices of various types have already been used. For example, propeller stirrers are used which are attached to an axle rotating in the interior of the bioreactor. These stirrers ensure a sufficient homogeneity of the cells in the culture medium when they rotate sufficiently quickly. However, the comparatively rapid rotation gives rise to the danger that sensitive cells, especially adherent cells on microcarriers, are damaged.

European Patent Specification No. 0,053,869 describes a stirrer device which is especially suitable for micro-carrier cultures of adherent cells in which a centrally suspended stirrer paddle in a fermentation vessel makes a circular oscillatory movement. However, such paddle stirrers are only suitable for comparatively small bioreactors.

Therefore, there is a need for a bioreactor which is also suitable for comparatively large volumes of cell culture (more than 10 liters), the stirring device of which ensures a homogeneous distribution of the cells in the culture medium without the cells being damaged.

SUMMARY OF THE INVENTION

Thus, according to the present invention, there is provided a bioreactor for culturing biological material capable of multiplication, especially cells securely adhering to microcarriers, with a vessel for a culture medium having means for controlling the environmental conditions in the culture medium and a stirring device for the homogeneous distribution of the cells in the culture medium which has a rotary drive and a rotation axle running in the interior of the vessel, wherein the stirring device has at least one flat stirrer blade fixed on to the rotation axle and inclined to the rotation axle.

BRIEF DESCRIPTION OF THE DRAWING

The FIGURE shows, in vertical cross-section, a bioreactor useable in the process according to this invention.

DETAILED DISCLOSURE

The stirrer blade is preferably a flat, circular plate, through the centre of which runs the rotation axle. On its surface, it can have projecting constructional elements or structures which are preferably so constructed that they do not have any sharp edges or corners and do not produce any turbulence in the culture medium. In its totality, it can also be undulated or have a surface construction which is other than completely flat. However, a smoothly flat, substantially plane surface on both sides of the surface is especially preferred.

The thickness of the blade can vary within comparatively great ranges but it must be planar in the sense that its planar extension is greater by a multiple than its material thickness. In general, for constructional and economic reasons, a material thickness is chosen which is not substantially greater than is necessary for the prevailing mechanical loadings.

In a bioreactor according to the present invention, a very rapid and complete homogenisation of the culture is already achieved with very low speeds of rotation of less than 50 r.p.m., preferably of less than 35 r.p.m. and more preferably of less than 20 r.p.m. At the same time, the biomaterial is treated very gently so that sensitive cells are not damaged.

An especially good homogenising effect is achieved when the stirrer blade has an angle of inclination to the rotation axle of 35° to 60° and when several stirrer blades are used which preferably rotate about the same rotation axle and with the same speed of rotation.

As already mentioned, the stirrer blades are preferably circular which additionally reduces the danger of damaging sensitive cells. However, under certain circumstances, a construction can be considered in which the edge of blades does not run exactly circularly. However, in every case, due to the rotating movement, a cylindrically-shaped region of the culture medium is engaged. The diameter of this region is referred to as the "effective diameter" of the stirrer blade.

The bioreactors are usually constructed with a substantially cylindrical shape with a rounded-off cylinder bottom. It has proved to be favourable when the effective diameter of the stirrer blade is at least 40%, preferably at least 50% and more preferably at least 60% of the inner diameter of the bioreactor.

The stirrer blades can be made from numerous different materials and especially of synthetic resins or alloyed steels. A material is preferably used to which the cultured cells do not adhere, polytetrafluoroethylene (Teflon) having proved to be especially useful.

The present invention will now be described in more detail with reference to the accompanying drawing which shows a bioreactor according to the present invention in vertical cross-section.

The illustrated bioreactor has a vessel 1 for the culture medium which vessel consists essentially of a cylindrical middle part 2, a lower cover 3 and an upper cover 4. Both covers are screwed with flanges on to the middle part 2 and are sealed by seals 5 and 6.

The vessel 1 stands on supporting columns 7. A temperature probe 8 is so arranged that the temperature of the culture medium can be measured. In operation, the vessel is substantially filled with culture medium 9. The surface of the culture medium is indicated by 10.

Apart from the temperature probe 8, further devices are provided for the control of the environmental conditions in the culture medium. In the Figure, this is shown by a dip tube 11 passing through the cover 4 which can be used, for example, for gassing the culture medium with air or oxygen. In the lower cover 3 of the vessel 1 are provided connection pipes 12 and 13 through which a tempering medium can be introduced and removed, which medium flows through a cooling or heating coil (not shown for the sake of clarity) in the interior of the vessel 1 so that, together with the temperature probe, a temperature regulation is possible.

Further devices for the control of the environmental conditions are usual in the case of bioreactors but, for the sake of clarity, are not shown in the Figure. For the observation of the actual state of the culture medium, there are used, for example, measurement probes for the determination of the pH value and of the oxygen and carbon dioxide partial pressures, as well as optical windows. For the control of the environmental conditions in the culture medium 9, there can be provided, for example, connections for the introduction or removal of substances (gases, nutrients, waste materials and the like). The multipurpose pipe 14 which can be seen in the cover 4 of the illustrated fermenter can, for example, serve such purposes. However, a reflux condenser with a filter for escaping gas can also be attached thereto.

The present invention is directed, in particular, to the stirring device placed in the illustrated bioreactor. It has stirrer blades 15 which are fixed centrally and non-torsionally on a rotation axle 16. The plane of the stirrer blades 15 is inclined at an angle of inclination alpha to the rotation axle. The fixing of the stirrer blades 15 on the rotation axle 16 is improved by a fixing piece 17. Between the lowermost stirrer blade 15 and the bottom of the vessel 1, a paddle stirrer 18 is also fixed non-torsionally on the rotation axle 16. The rotation axle 16 is driven by a rotary drive 19 in the usual way with an adjustable speed of rotation.

In the case of rotation of the rotation axle 16, the culture medium is driven by the rotating stirrer blades and placed in a complex movement. Details of this movement cannot be given. However, practical experiments have shown that, with the help of the obliquely-positioned stirrer blades according to the present invention, there is achieved a surprisingly rapid and complete homogenisation of the culture medium 9. Several stirrer blades are thereby preferably used, the dimensioning and positioning of which can be carried out on the basis of the following remarks.

The angle of inclination alpha has proved to be comparatively non-critical. Angles between about 35° and about 60° give rise to good results. The number and inclination of the stirrer blades 15 should be adapted to the dimensions of the vessel 1 of the bioreactor. The higher the bioreactor, the more blades must be used.

The recommended distance a between adjacent stirrer blades thereby depends upon their effective diameter D and the angle of inclination alpha. This may, therefore, be explained in that the range encompassed by a stirrer blade in the axial direction of the rotation axle 16 is the greater the smaller is the angle of inclination alpha and the greater is the effective diameter D of the stirrer blade. The points of the edges of the stirrer blades which, in comparison with the centre, are most displaced in the axial direction are indicated by 15b and 15c in the Figure. The range of the culture medium encompassed by a stirrer blade is, in the axial direction, substantially limited by the rotating extreme points 15b and 15c, i.e. by, in each case, a plane running through these points vertically to the axle 16. It has been shown that a good and effective mixing up of culture medium with stirrer blades is achieved when the distance a of adjacent stirrer blades is at most about twice as great and at least about half as great as the distance b of the extreme points of the stirrer blade edge most staggered with regard to one another in the axial direction. This range of advantageous blade distances is astonishingly great and proves the outstanding mixing action of the stirrer blades. Quite especially good results are achieved when the stirrer blade distance a is at most 50% greater than the distance b.

The propeller stirrer 18 serves to stir up any cells possibly sitting on the bottom of the vessel so that they are taken up in the stirring region of the stirrer blades 15. The propeller stirrer 18 is preferably so constructed that it forces downwardly the liquid when the rotation axle 16 is rotating. Instead of the propeller stirrer, there can also be used some other stirring element rotating or revolving near the bottom of the container, for example a paddle stirrer.

The embodiment of the present invention illustrated in the Figure is constructed rotation symmetrically, i.e. the middle part 2 of the vessel 1, the stirrer blades 15 and the axle 16 are, in each case, preferably circular and coaxial to one another. Such a rotation-symmetrical construction is especially simple and usual in the case of bioreactors. However, in special cases, a deviation herefrom can be expedient, for example, the rotation axle 16 can be displaced with regard to the central axis of the vessel 1. In this case, the statements of dimensioning referred to the rotation-symmetrical construction apply correspondingly.

In the case of the illustrated embodiment, the stirrer blades are all of the same size and fixed at equal distances parallel to one another on a common rotation axle in a non-torsional manner. This construction is simple and economic. However, for special reasons, it can also be expedient to use the obliquely-positioned stirrer blades in some other manner, for example in an arrangement in which they admittedly sit on a common axle but do not run parallel to one another or in which they even sit on different axles, which can be coaxial or non-coaxial to one another, so that their speeds of rotation can also be different.

What is claimed is:

1. A process for culturing biological material capable of multiplication, which comprises the steps of:
homogeneously suspending the biological material in a culture medium;
placing said culture medium in a bioreactor comprising a vessel having a top wall and a bottom wall, means for controlling environmental conditions in the culture medium, and stirring means for the homogeneous distribution of the biological material in the culture medium, the stirring means having a rotation axle defining an axial direction and attached to a rotary drive means for driving the stirring means, said stirring means extending into and rotating in the interior of the vessel and comprising a plurality of stirrer blades in the form of plates affixed at adjacent points along the rotation axle with an angle of inclination toward said rotation axle, each stirrer blade having at its edge two extreme points displaced in the axial direction from the point at which the plate is fixed to the rotation axle, these extreme points having a predetermined distance in axial direction from each other, and wherein said points at which said stirrer blades are affixed to said rotation axle are separated from each other by a distance in the range of at least about half as great as said predetermined distance between said extreme points; and causing said stirrer blades to rotate, thereby keeping said biological material in homogeneous suspension while the biological material is multiplying.

2. A process according to claim 1, in which, in the vessel, the angle of inclination of the stirrer blade to the rotation axle is in the range of 35° to 60°.

3. A process according to claim 1, wherein the points at which the stirrer blades are affixed to said rotation axle are separated from each other by a distance in the range of at most about twice as great as said predetermined distance between said extreme points.

4. A process according to claim 1, in which the vessel has a cyclindrical shape and the stirrer blades have an effective diameter of at least 40% of the interior diameter of said vessel.

5. A process according to claim 4, in which the effective diameter of the stirrer blade is at least 50% of the interior diameter of said vessel.

6. A process according to claim 5, in which the effective diameter of the stirrer blade is at least 60% of the interior diameter of said vessel.

7. A process according to claim 1, in which, in the vessel, the stirring means further comprises a stirrer element attached to the rotation axle and rotating in a region near the bottom wall of said vessel.

8. A process according to claim 7, in which the stirrer element is a propeller stirrer.

9. A process according to claim 1, in which, in the vessel, the stirrer blades further comprise a material to which the biological material does not substantially adhere.

10. A process according to claim 9, in which the material comprising said stirrer blades is polytetrafluoroethylene.

11. A process according to claim 1, in which, in the vessel, the rotary drive means is capable of rotating the rotation axle at a speed of less than 50 r.p.m.

12. A process according to claim 11, in which the rotary drive means is capable of rotating the rotation axle at a speed of less than 35 r.p.m.

13. A process according to claim 12, in which the rotary drive means is capable of rotating the rotation axle at a speed of less than 20 r.p.m.

* * * * *